(12) United States Patent
Fleischer et al.

(10) Patent No.: US 9,521,957 B2
(45) Date of Patent: Dec. 20, 2016

(54) HAND-HELD DEVICE FOR SELF-MEASUREMENT AND RECORDING OF A HEART RATE VARIABILITY EXAMINATION

(75) Inventors: Jesper Fleischer, Højbjerg (DK);
Martin Snejbjerg Jensen, Århus C (DK)

(73) Assignee: MEDICUS ENGINEERING APS, Aarhus C (DK)

(*) Notice: Subject to any disclaimer, the term of this patent is extended or adjusted under 35 U.S.C. 154(b) by 0 days.

(21) Appl. No.: 12/923,015

(22) Filed: Aug. 30, 2010

(65) Prior Publication Data

US 2011/0066011 A1    Mar. 17, 2011

Related U.S. Application Data

(62) Division of application No. 11/667,470, filed as application No. PCT/DK2005/000611 on Sep. 27, 2005, now abandoned.

(30) Foreign Application Priority Data

Nov. 10, 2004 (DK) .................. 2004/01734

(51) Int. Cl.
*A61B 5/00* (2006.01)
*G06F 19/00* (2011.01)
(Continued)

(52) U.S. Cl.
CPC ....... *A61B 5/02438* (2013.01); *A61B 5/02405* (2013.01); *A61B 5/0404* (2013.01);
(Continued)

(58) Field of Classification Search
CPC ........... A61B 5/02; A61B 5/40; A61B 5/4035; A61B 5/0205; A61B 5/02438; A61B 5/0404; A61B 5/08; G06F 19/34; G06F 19/3406
(Continued)

(56) References Cited

U.S. PATENT DOCUMENTS 4,417,586 A   11/1983   Jewett
4,825,874 A   5/1989   Uhlemann
(Continued)

FOREIGN PATENT DOCUMENTS

DE   201 19 962   5/2002
EP   917069   5/1999
(Continued)

OTHER PUBLICATIONS

International Search Report dated Feb. 14, 2006 for corresponding International Application No. PCT/DK2005/000611.
(Continued)

*Primary Examiner* — William Thomson
*Assistant Examiner* — Marie Archer
(74) *Attorney, Agent, or Firm* — Pillsbury Winthrop Shaw Pittman LLP

(57) ABSTRACT

The invention relates to a method and device for recording and presentation of physiological parameters, which can include both blood pressure and heart pulse. Information about the heart pulse is derived from a recorded blood pressure signal, whereby the need for e.g. an external ECG measurement device is eliminated. It is likewise a part of the invention that a blood pressure measurement is used for the derivation of data such as Heart Rate Variability (HRV) and/or baroreflex sensitivity (BRS) values.

9 Claims, 9 Drawing Sheets

(51) Int. Cl.
*A61B 5/024* (2006.01)
*A61B 5/0404* (2006.01)
*A61B 5/08* (2006.01)
*A61B 5/021* (2006.01)

(52) U.S. Cl.
CPC .............. *A61B 5/08* (2013.01); *A61B 5/4035* (2013.01); *A61B 5/6887* (2013.01); *A61B 5/72* (2013.01); *A61B 5/74* (2013.01); *G06F 19/34* (2013.01); *G06F 19/3406* (2013.01); *A61B 5/0002* (2013.01); *A61B 5/021* (2013.01); *A61B 2560/0468* (2013.01)

(58) Field of Classification Search
USPC ................ 600/300–301, 363–365, 373–374, 600/377–379, 382–384, 386–394, 481, 600/485, 500–503, 509, 515–519, 600/529–531, 544–547, 549, 587–595; 128/920–925; 607/1–76
See application file for complete search history.

(56) References Cited

U.S. PATENT DOCUMENTS

| | | | |
|---|---|---|---|
| 5,183,051 A | | 2/1993 | Kraidin et al. |
| 5,265,615 A | | 11/1993 | Frank et al. |
| 5,299,119 A | | 3/1994 | Kraf et al. |
| 5,337,753 A | * | 8/1994 | Lekhtman ................ 600/519 |
| 5,718,235 A | | 2/1998 | Golosarsky et al. |
| 5,865,758 A | | 2/1999 | Louzianine |
| 6,120,442 A | | 9/2000 | Hickey |
| 6,421,557 B1 | * | 7/2002 | Meyer ........................ 600/516 |
| 6,569,094 B2 | | 5/2003 | Suzuki et al. |
| 6,790,178 B1 | * | 9/2004 | Mault .............. A61B 5/0011 128/903 |
| 8,185,181 B2 | | 5/2012 | Feldman et al. |
| 9,050,041 B2 | | 6/2015 | Feldman et al. |
| 2002/0022785 A1 | | 2/2002 | Romano |
| 2002/0058877 A1 | * | 5/2002 | Baumann et al. ............ 600/485 |
| 2002/0143576 A1 | | 10/2002 | Nolvak et al. |
| 2003/0097158 A1 | * | 5/2003 | Belalcazar ..................... 607/32 |
| 2003/0120164 A1 | | 6/2003 | Nielsen et al. |
| 2003/0204145 A1 | * | 10/2003 | Manolas ..................... 600/513 |
| 2005/0251055 A1 | * | 11/2005 | Zhirnov et al. .............. 600/509 |
| 2007/0179385 A1 | * | 8/2007 | Cho et al. ..................... 600/485 |

FOREIGN PATENT DOCUMENTS

| | | |
|---|---|---|
| EP | 1103217 | 5/2001 |
| WO | WO 92/06633 | 4/1992 |

OTHER PUBLICATIONS

Barros et al., "Heart Instantaneous Frequency (HIF): An Alternative Approach to Extract Heart Rate Variability," IEEE Trans. *On Bio-med Eng.*, vol. 48, No. 8, pp. 850-855 (Aug. 2001).

De Angelis et al., "Exercise Reverses Peripheral Insulin Resistance in Trained L-NAME-hypertensive rats," *Hypertension*, vol. 34, No. 4, pt. 2, pp. 768-772 (Oct. 1999).

Supplementary European Search Report dated Jul. 24, 2009 for corresponding European Application No. 05786636.

* cited by examiner

Diagnostic tests for cardiovascular autonomic neuropathy

Resting heart rate
100 beats/minute is abnormal

Beat-to-beat heart rate variation
The patient should abstain from drinking coffee overnight
Test should not be performed after overnight hypoglycemic episodes
When the patient lies supine and breathes 6 times per minute, a difference in heart rate of less than 10 beats/minute is abnormal
An expiration: inspiration R-R ratio > 1.17 is abnormal

Heart rate response to standing
The R-R interval is measured at beats 15 and 30 after the patient stands
A 30:15 ratio of less than 1.03 is abnormal

Heart rate response to Valsalva maneuver
The patient forcibly exhales into the mouthpiece of a manometer, exerting a pressure of 40 mm Hg for 15 seconds
A ratio of longest to shortest R-R interval of less than 1.2 is abnormal

Systolic blood pressure response to standing
Systolic blood pressure is measured when the patient is lying down and 2 minutes after the patient stands
A fall of more than 30 mm Hg is abnormal
A fall of 10 to 29 mm Hg is borderline

Diastolic blood pressure response to isometric exercise
The patient squeezes a handgrip dynamometer to establish his or her maximum
The patient then squeezes the grip at 30% maximum for 5 minutes
A rise of less than 16 mm Hg in the contralateral arm is abnormal

FIG. 3

HAND-HELD DEVICE FOR SELF-MEASUREMENT AND RECORDING OF A HEART RATE VARIABILITY EXAMINATION

This application is a divisional application of U.S. application Ser. No. 11/667,470, filed on Sep. 11, 2008, now abandoned which is a national phase application of PCT International No. PCT/DK2005/000611, filed on Sept. 27, 2005, which claims priority to Danish Patent Application No. PA 2004/01734, filed on Nov. 11, 2004, in the Denmark Patent Office, the contents of each of which are incorporated herein by reference in their entirety.

The invention relates to a method of recording and presenting physiological data from humans or animals.

Moreover the invention relates an apparatus for recording and presenting physiological data from humans or animals.

It is known to perform measurings on humans or animals in order to deduce information about the physiological state of the measuring objects. Blood pressure is among the physiological data, which in this connection, is often registered.

The blood pressure is routinely being measured both in healthy people, e.g. athletes as a part of optimizing training activities, as well as in ill people, where the information about the blood pressure is often a significant parameter in the clinical diagnosis.

The blood pressure is often measured as one of several physiological parameters, which combined can provide better and more clearly defined information about the physiological state of the measuring object.

One of the most important additional physiological data, which is often collected as an addition to the blood pressure determination, is information about the heart pulse, typically including recording of the so-called electrocardiographic signal (ECG)

Among the parameters, which are often desired to be derived in relation with assessment of the physiological state, is the so-called Heart Rate Variability (HRV), which is defined as the distance in milliseconds from heartbeat to heartbeat.

Another important parameter, which directly connects information about blood pressure and heart pulse, is the so-called baroreflex sensitivity (BRS), which is defined as the change in the distance in milliseconds from heartbeat to heartbeat as a result of change in the so-called systolic pressure and is thereby measured in the unit [ms/mmHg].

As a result of the still more intense physiological and medical research there is a still increasingly demand for linkage of different physiological data such as blood pressure and heart pulse.

With the hitherto known technique these compound physiological data have been collected with a number of separate measuring instruments, which have separately measured the single physiological data such as blood pressure and heart pulse.

It has been found, however, that this known technique involves some drawbacks.

One of these drawbacks originates from the fact that the measuring procedures become complicated since there is often simultaneously being used several measuring devices.

Besides the difficult and time-consuming aspect of getting several independent measurement devices to work simultaneously, the possibilities of erroneous measurement will statistically increase along with the complexity of the measurements.

Moreover the analysis work is made inconvenient since data from different measurement devices must be integrated, including scaled and time-synchronized before the data processing can be completed.

Besides being time-consuming and thereby adding to costs as well as being subjected to an increased risk of errors, the compound measurements with use of several different measurement devices is also causing an increased discomfort for the people, who are going to be subjected to measurements.

The complexity of the measurements also means that the measurements must in practice be carried out in a laboratory environment, despite the measurements would typically have had a higher relevance in the assessment of the physiological state if they had been performed in the persons' daily environments.

It is therefore a purpose of the invention to improve the known method and the known apparatus.

The object of the invention is achieved by a method described herein, which is characterized in that the method uses a measurement device, which can emit an electric signal proportional to the blood pressure of the measuring object, as well as being provided with technical means such as a digital signal processor for calculation of data such as Heart Rate Variability (HRV) and baroreflex sensitivity (BAS) values, as well as being provided with interface electronics for connection of additional signaling units such as pressure transducers and manometers, and being provided with algorithms for user control, calculation and data presentation of examination sequences such as: resting heart rate [0020] beat-to-beat heart rate variation [0021] heart rate response to standing [0022] heart rate response to Valsalva maneuver [0023] systolic blood pressure response to standing [0024] diastolic blood pressure response to isometric exercise.

In this way it thus becomes possible with only a single measurement device to measure inter-related physiological data, which includes both the blood pressure and the heart pulse.

As mentioned the invention also relates to an apparatus.

This apparatus is characterized in that the apparatus emits an electric signal, which is proportional to the blood pressure of the measuring object, as well as being provided with means such as a digital signal processor for recording and processing of the blood pressure signal, as well as algorithms for derivation of data such as Heart Rate Variability (HRV) and/or baroreflex sensitivity (BRS) values.

Hereby it thus becomes possible, solely on the basis of measuring the blood pressure, to derive information about the heart pulse and thereby calculate HRV as well as BRS values.

It may moreover be a characteristic feature of the invention that the device is provided with means for data recording such as pressure transducers, including ones for recording of exhalation air pressure and hand grip squeeze pressure, as well as algorithms for user control and data processing for carrying out test- and/or examination sequences, as well as means such as display and/or sound device(s) such as e.g. loudspeakers for guiding a user and data presentation.

Hereby the advantage is achieved that physiologically connected data can be measured solely by using a single measurement device, which can besides, via an appropriate data presentation medium such as a display, guide the user through possible test(s) and exercises, which are included in a specific type of examination.

Further embodiments of the invention are described herein.

The invention will now be explained more fully with reference to the drawings, in which:

FIG. 3 shows a list of standardized physiological tests where both blood pressure and heart pulse are included.

Figure 1:
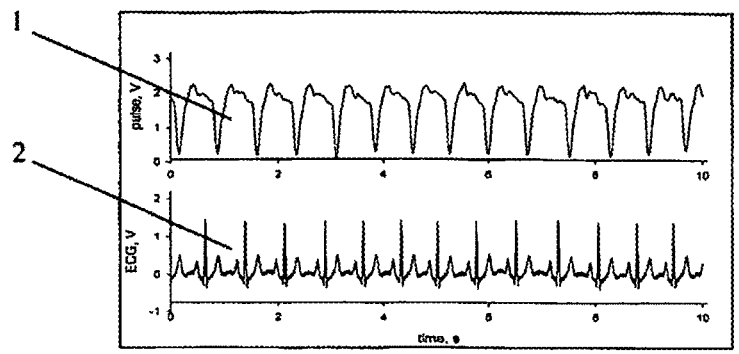
FIG. 1 shows correlation between blood pressure signal and ECG signal from the heart of a measurement object.

In FIG. 1 is with 1 shown the blood pressure signal, as it can be measured from e.g. a human by using a blood pressure gauge, characterized in that it contains a transducer, which can submit an electric signal proportional to the registered blood pressure.

The vertical axis shows the amplitude of the blood pressure (e.g. scaled in volt (V)), while the horizontal axis shows the time sequence (e.g. scaled in seconds (s)).

With 2 is shown the ECG signal from the same measurement object, from where 1 shows the blood pressure. The ECG signal 2 is shown with the same horizontal timescale, as the blood pressure 1, and the vertical axis for the ECG signal likewise specifies the amplitude of this signal.

It is common clinical practice to express the heart pulse on the basis of the distance between the so-called R signal components (the dominating peak) in the ECG signal based on the formula: Pulse=60/(R-R distance measured in seconds).

As it is seen from the two curve sequences for respectively blood pressure and the ECG, these proceed simultaneously over time.

Experiments have shown, that it is possible by using an appropriate signal processing of the blood pressure signal to derive the heart pulse information from the blood pressure signal with a precision, which is comparable with the calculation based on the RR interval from the ECG signal.

When the heart pulse is derived on the background of the blood pressure signal, the ECG measurement device or similar special measurement devices can be excluded for physiological examinations, which link blood pressure and heart pulse.

Figure 2:
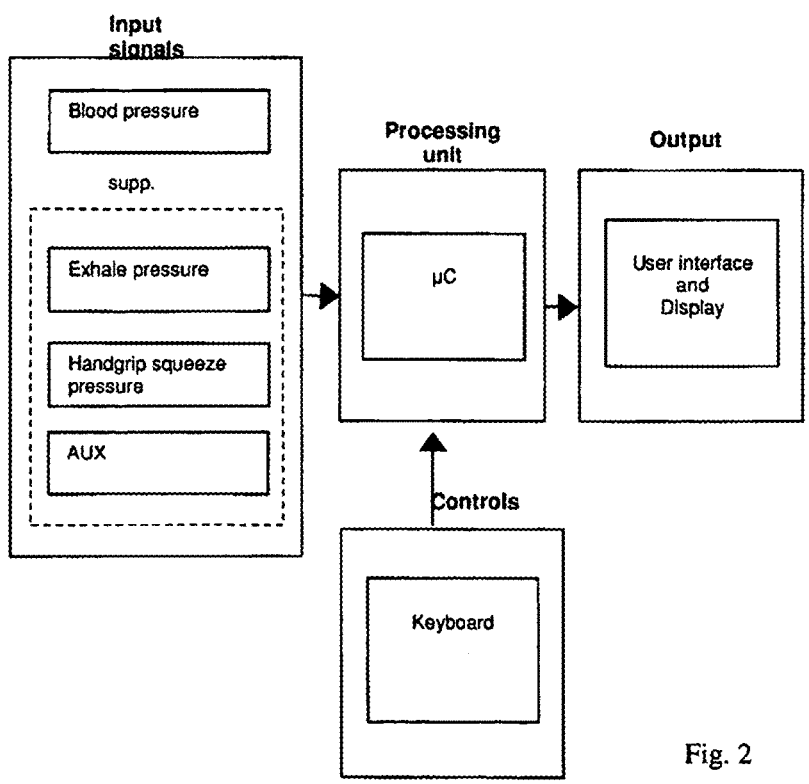
FIG. 2 shows a block diagram for the structure of an apparatus for measurement of compound physiological data, which involves both blood pressure and heart pulse.
Figure 4:
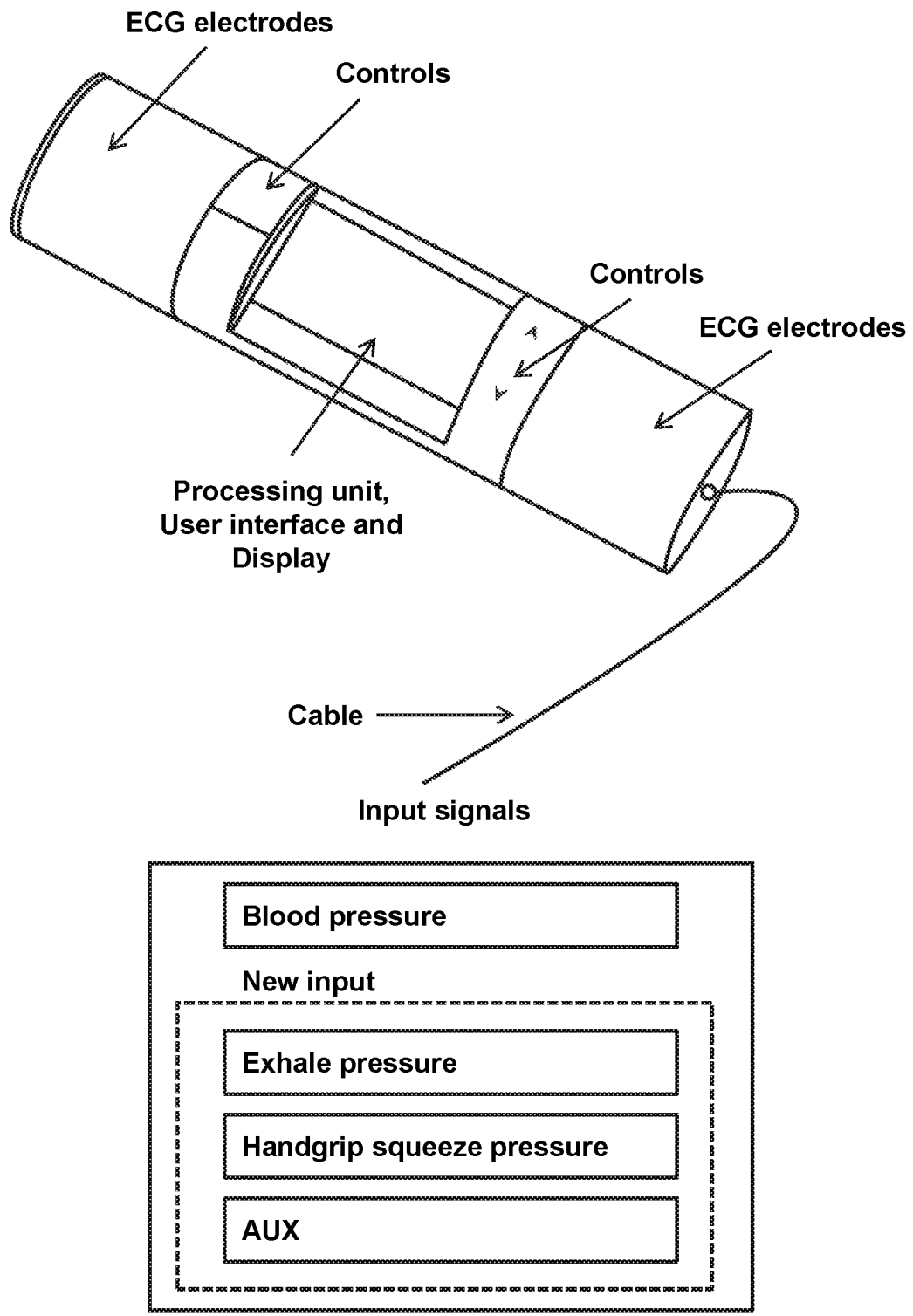
FIG. 4 shows attachment of input signal mediums to a central calculation-, interface- and display unit.
Figure 5:
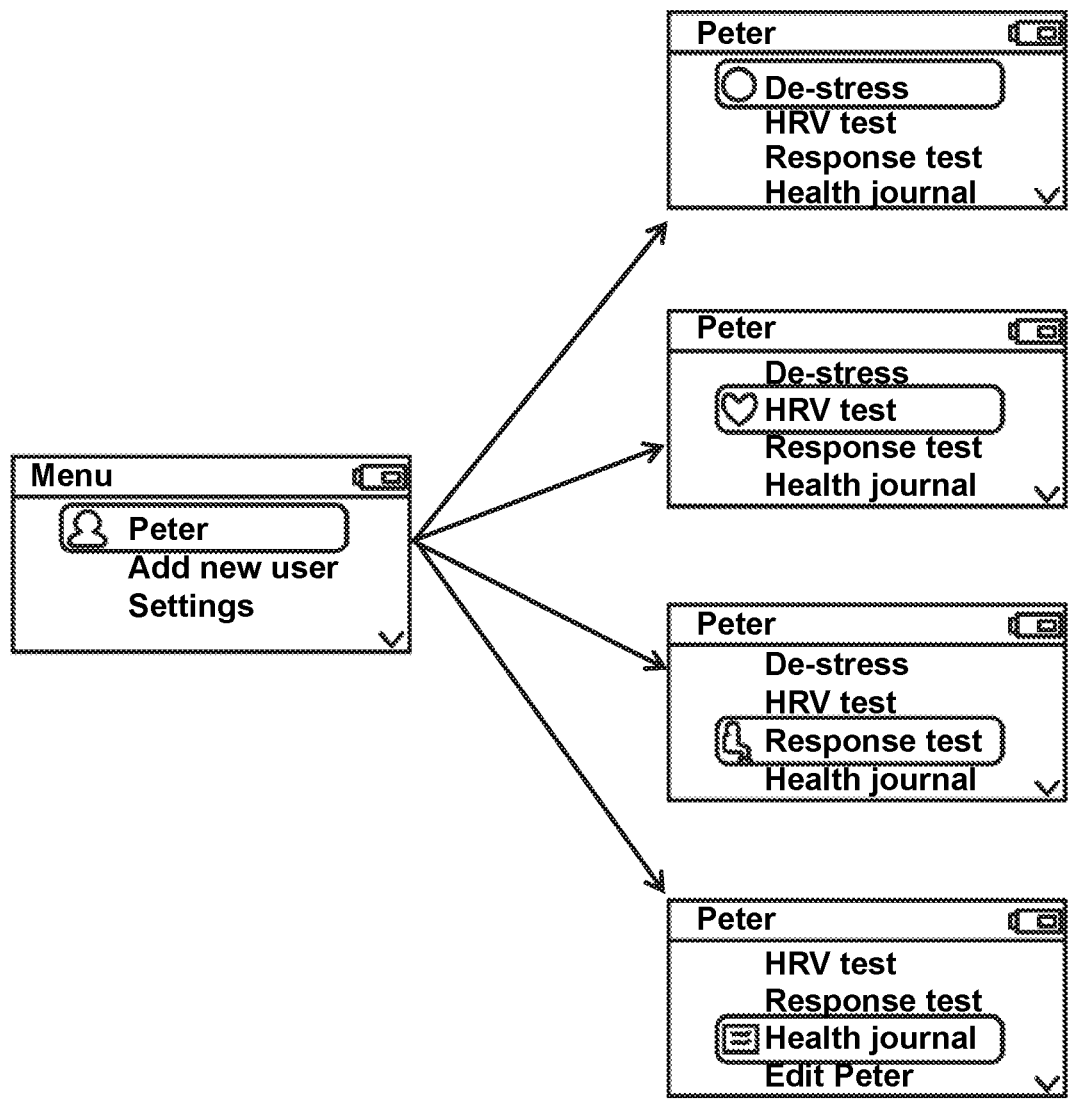
FIG. 5 shows an example of visual display-guiding of examination choice.
Figure 6:
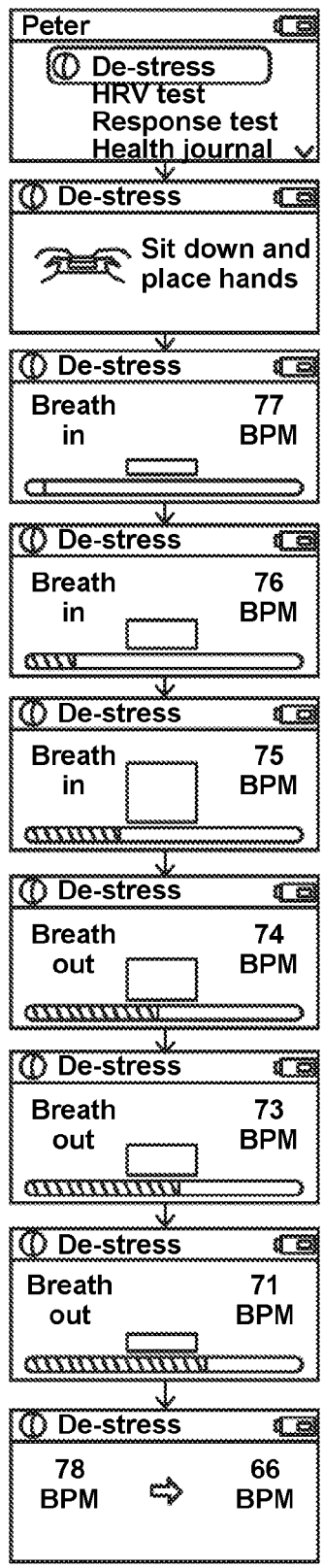
FIG. 6 shows an example of visual display-guiding of a selected so-called de-stress examination type.
Figure 7:
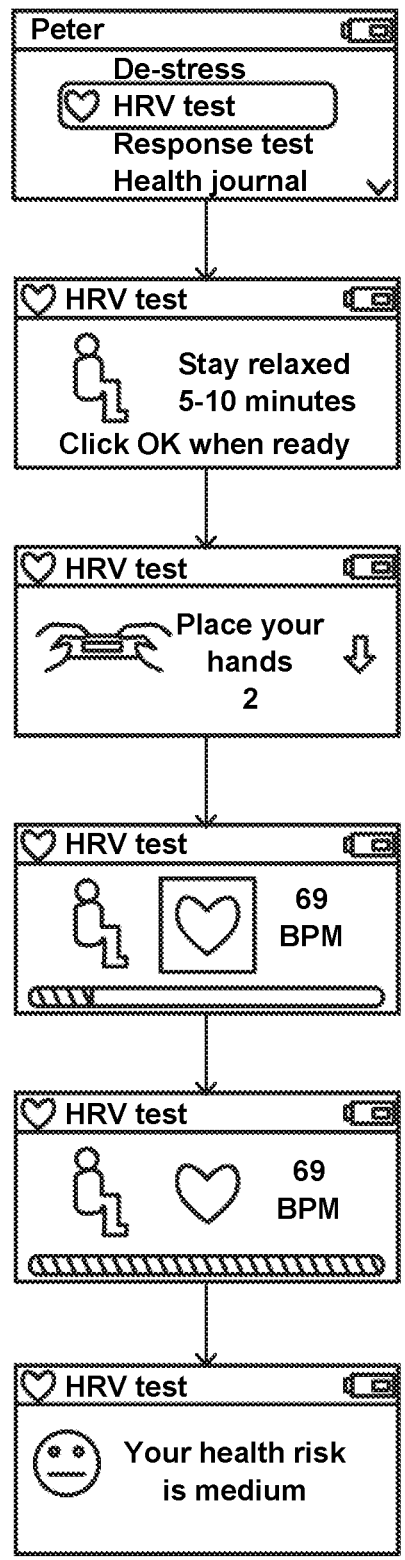
FIG. 7 shows an example of visual display-guiding of an selected so-called HRV test examination type.
Figure 8:
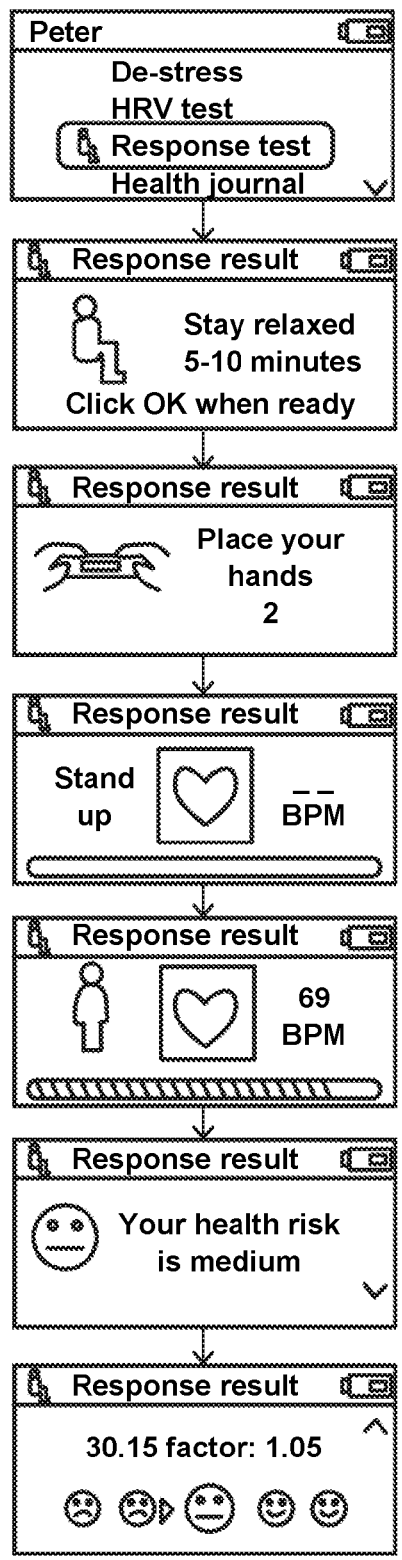
FIG. 8 shows an example of visual display-guiding of a selected so-called response test examination type.
Figure 9:
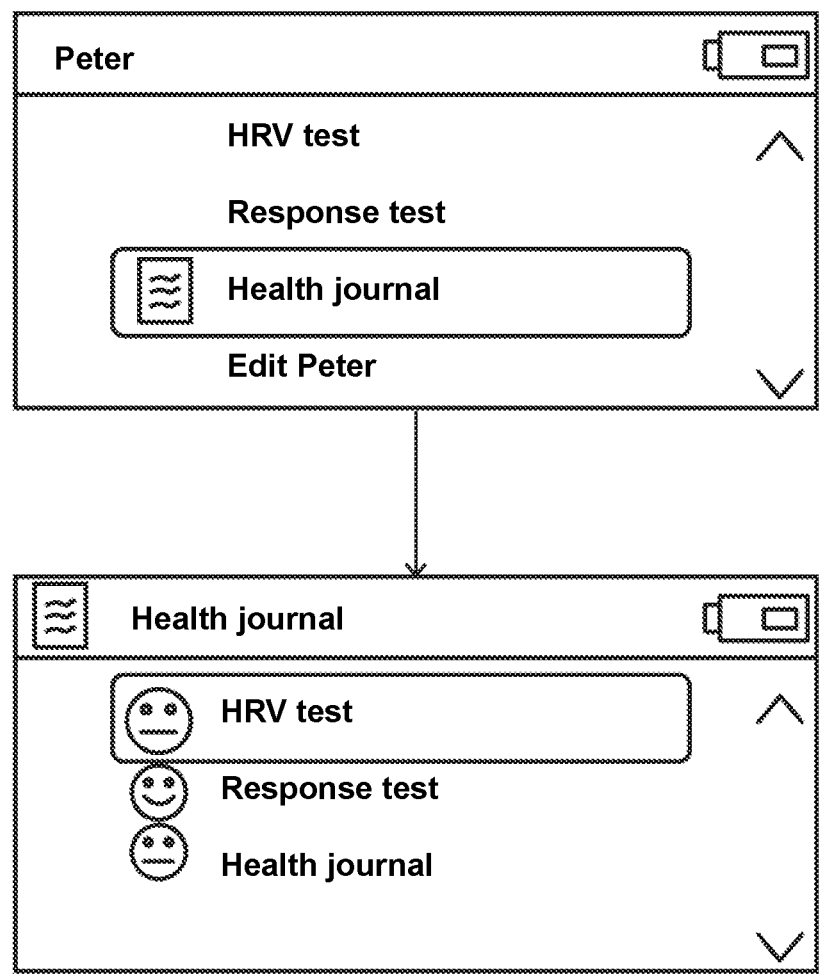
FIG. 9 shows an example of visual display-guiding of a selection of a so-called health journal.
Figure 10:
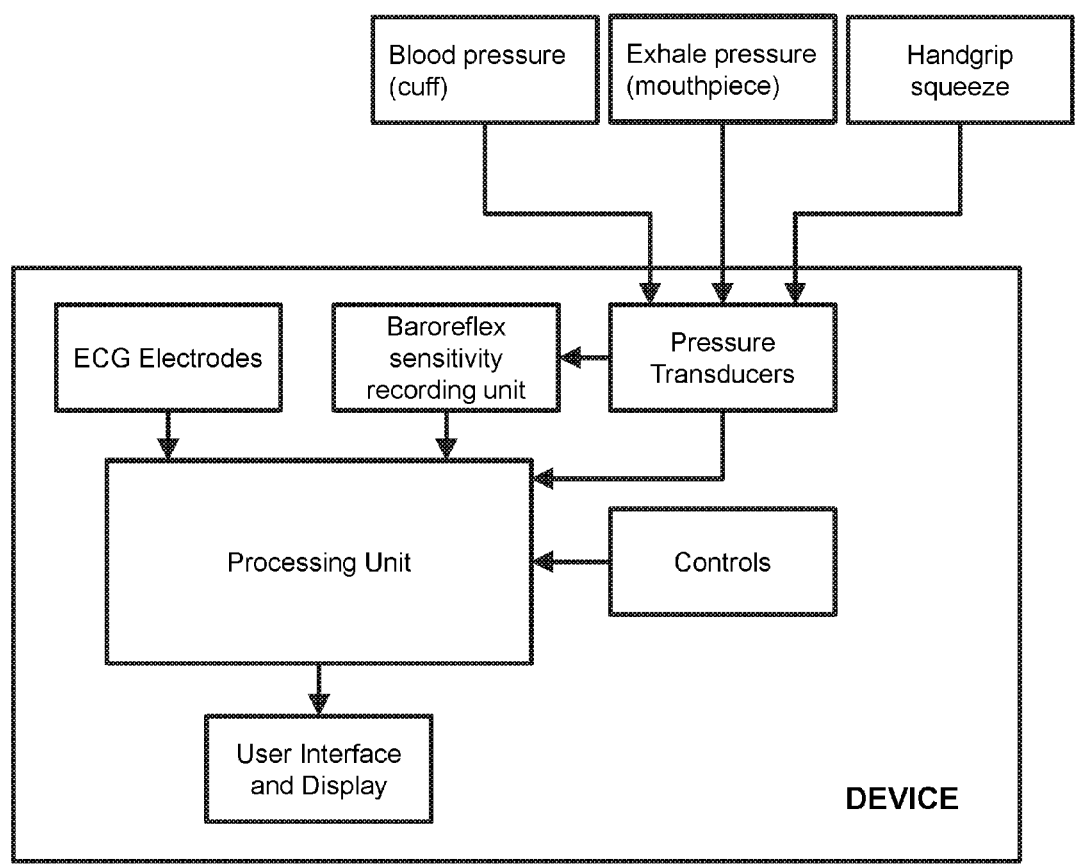
FIG. 10 shows an example block diagram with respect to the measurement device in FIG. 4.

In FIG. 2 is shown a block diagram, which basically describes the hardware structure of an integrated measurement apparatus, which can be used for physiological examinations, which involves data for both blood pressure and heart pulse.

The measurement device consists of a central processing unit marked µC, which can in practice be a digital signal processor or another similar component device.

The processing unit µC is controlled by a control unit, which can e.g. be a keyboard or a number of pushbuttons.

To the central process unit µC is also connected an output medium, which can e.g. be a display or a monitor including one, which includes a sound device.

The central processor µC moreover receives data from some input signals, including data from a blood pressure measuring unit, from which both blood pressure and the heart pulse can be derived.

The central processor µC can moreover be provided with additional input signal units, which can give information about e.g. exhale pressure and handgrip squeeze pressure as well as one or more additional aux signal input units for other specific measurement data.

By application of the shown hardware configuration the same, in the principle simple, measurement device can be used for recording and presentation of many different important physiological examinations.

In FIG. 3 is shown an overview of a number of examinations with physiological relevance, which the apparatus presented in FIG. 2 can be used to carry out.

The specified examinations include: [0058] resting heart rate [0059] beat-to-beat heart rate variation [0060] heart rate response to standing [0061] heart rate response to Valsalva maneuver [0062] systolic blood pressure response to standing [0063] diastolic blood pressure response to isometric exercise.

All the shown examinations can be carried out with the measurement device shown in FIG. 2, that is without parallel application of ECG or another specific device for measuring heart pulse.

As it will appear from FIG. 3, there is connected a specific procedure to several of the stated examination methods, which must be followed during the data recording.

It is a part of the present invention that the apparatus/device as shown in FIG. 2 contains algorithms, which can guide the user, including both the measurement object and the user of the device, to run and complete a specific examination correctly.

As an example of this the so-called Heart rate response to Valsalva maneuver examination can be mentioned, which is based on that the examined person exhales air with a pressure of 40 mmHg in a period of 15 seconds.

Here, the measuring apparatus shown in FIG. 2 will be able to graphically represent both the pressure, with which the person exhales and thereby guide the person to the correct pressure, as well as show the lapse of time and show the remaining time in which the person must maintain the correct exhalation pressure.

FIG. 5 to FIG. 9 shows examples of how the user as well as the person being examined via a display can be guided through all the phases in a selected examination type.

After the data collection the measuring device can, controlled by implemented calculation algorithms, subsequently derive the desired results and show these on the display unit or via a wireless data communication unit transmit these to an external unit such as a computer including an electronic patient record.

With integration of a wireless data communication unit it will also be possible to record data wirelessly from the object being measured, so that wires etc. connected to the measuring object can be reduced to a minimum.

With the simplified measuring apparatus in accordance to the invention, it will be possible to move even complex physiological examinations away from dedicated examination laboratories and out in the environments, where the examined are normally to be found, which will be able to improve the physiological information.

The invention is not limited to the methods and devices, which are directly described or illustrated in this present document, but also includes all methods and devices/apparatus, which can indirectly be inferred from the text or the figures or a combination of these.

What is claimed is:

1. A hand-held measurement device for facilitating patient self-measuring and recording, the hand-held measurement device comprising:
a housing, and a pressure transducer, a display, electrocardiogram (ECG) electrodes, and a processor, each of which is within the housing, the processor being configured to:
measure, via the pressure transducer, an exhalation pressure of a patient during a time period associated with an examination;
cause a first graphical component indicating the exhalation pressure measurement to be presented on the display such that the first graphical component is continuously updated in real-time, as the exhalation pressure is being measured, until at least the end of the time period associated with the examination;
cause a second graphical component indicating a remaining time of the time period to be presented on the display such that the second graphical component is continuously updated in real-time, as the exhalation pressure is being measured, until at least the end of the time period associated with the examination;
measure, via the ECG electrodes, a heart rate of the patient during the time period associated with the examination; and
calculate heart rate variability of the time period associated with the examination based on the heart rate measurement and cause a graphical component indicating the heart rate variability to be presented on the display.

2. The hand-held measurement device according to claim 1, wherein the processor is further configured to:
measure, via the pressure transducer, a blood pressure of the patient during the time period associated with the examination.

3. The hand-held measurement device according to claim 1, wherein the processor is further configured to:
measure, via the pressure transducer, a hand grip squeeze pressure of the patient during the time period associated with the examination.

4. The hand-held measurement device according to claim 1, further comprising a baroreflex sensitivity recording unit.

5. The hand-held measurement device according to claim 1, further comprising a plurality of push buttons configured to provide control signals to the processor.

6. The hand-held measurement device according to claim 1, wherein the hand-held measurement device is adapted to simultaneously measure pressure and ECG signals.

7. The hand-held measurement device according to claim 1, wherein the processor is further configured to:
cause step-by-step instructions for using the hand-held measurement device to perform patient self-measuring to be presented on the display during the examination and prior to the time period associated with the examination.

8. The hand-held measurement device according to claim 1, wherein the processor is further configured to:
cause step-by-step instructions for using the hand-held measurement device to perform patient self-measuring to be presented on the display prior to and during the time period associated with the examination.

9. The hand-held measurement device according to claim 1, wherein the processor is further configured to:
cause one or more results of the examination to be presented on the display subsequent to the time period associated with the examination.

* * * * *